(12) United States Patent
Chang et al.

(10) Patent No.: US 6,538,162 B2
(45) Date of Patent: Mar. 25, 2003

(54) METHOD FOR CONVERTING ALKANES TO OXYGENATES

(75) Inventors: Clarence D. Chang, Princeton, NJ (US); Jose G. Santiesteban, Bethlehem, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/772,775

(22) Filed: Jan. 30, 2001

(65) Prior Publication Data

US 2002/0103402 A1 Aug. 1, 2002

(51) Int. Cl.[7] .................. C07C 41/09; C07C 27/14; C07C 27/16
(52) U.S. Cl. .................. 568/671; 568/877
(58) Field of Search .................. 568/671, 877

(56) References Cited

U.S. PATENT DOCUMENTS

| | | | |
|---|---|---|---|
| 2,110,816 A | 6/1938 | Pelc | 260/156 |
| 2,492,983 A * | 1/1950 | Grosse et al. | 558/39 |
| 3,898,057 A | 8/1975 | Moller et al. | 48/197 R |
| 3,950,270 A | 4/1976 | Paynter et al. | 252/464 |
| 4,025,571 A | 5/1977 | Lago | 260/668 D |
| 4,025,572 A | 5/1977 | Lago | 260/668 D |
| 4,025,575 A | 5/1977 | Chang et al. | 260/682 |
| 4,083,888 A | 4/1978 | Caesar et al. | 200/682 |
| 4,083,889 A | 4/1978 | Caesar et al. | 260/682 |
| 4,199,533 A | 4/1980 | Benson | 585/500 |
| 4,296,266 A | 10/1981 | Wunder et al. | 585/640 |
| 4,324,940 A | 4/1982 | Dessau | 585/466 |
| 4,374,295 A | 2/1983 | Lee | 585/640 |
| 4,423,273 A | 12/1983 | Hoelderich et al. | 585/640 |
| 4,433,188 A | 2/1984 | Hoelderich et al. | 585/640 |
| 4,433,189 A | 2/1984 | Young | 585/640 |
| 4,434,314 A | 2/1984 | Hoelderich et al. | 585/640 |
| 4,440,871 A | 4/1984 | Lok et al. | 502/214 |
| 4,441,990 A | 4/1984 | Huang | 208/111 |
| 4,480,145 A | 10/1984 | Brennan et al. | 585/640 |
| 4,496,786 A | 1/1985 | Santilli et al. | 585/640 |
| 4,499,327 A | 2/1985 | Kaiser | 585/640 |
| 4,523,040 A * | 6/1985 | Olah | 568/671 |
| 4,547,616 A | 10/1985 | Avidan et al. | 585/640 |
| 4,550,217 A | 10/1985 | Graziani et al. | 585/324 |
| 4,616,098 A | 10/1986 | Hoelderich et al. | 585/640 |
| 4,665,268 A | 5/1987 | Lee et al. | 585/640 |
| 4,677,242 A | 6/1987 | Kaiser | 585/638 |
| 4,677,243 A | 6/1987 | Kaiser | 585/638 |
| 4,698,452 A | 10/1987 | Le Van Mao et al. | 585/640 |
| 4,752,651 A | 6/1988 | Kaiser | 585/640 |
| 4,767,886 A | 8/1988 | Kawamura et al. | 585/640 |
| 4,777,321 A | 10/1988 | Harandi et al. | 585/640 |
| 4,861,938 A | 8/1989 | Lewis et al. | 585/640 |
| 4,912,281 A | 3/1990 | Wu | 585/640 |
| 5,095,163 A | 3/1992 | Barger | 585/640 |
| 5,097,090 A | 3/1992 | Beck | 568/842 |
| 5,191,141 A | 3/1993 | Barger et al. | 585/640 |
| 5,191,142 A | 3/1993 | Marshall et al. | 585/640 |
| 5,306,855 A * | 4/1994 | Periana et al. | 560/302 |
| 5,714,662 A | 2/1998 | Vora et al. | 585/640 |
| 5,714,663 A | 2/1998 | Serrand et al. | 585/648 |
| 6,040,257 A | 3/2000 | Drake et al. | 502/64 |

FOREIGN PATENT DOCUMENTS

| | | | |
|---|---|---|---|
| EP | 0026 041 | 4/1981 | |
| EP | 0 882 692 | 12/1998 | |
| WO | WO 99/24383 | * 5/1999 | C07C/29/48 |

OTHER PUBLICATIONS

Joseph Haggin, Methane Conversion: Two new direct oxidation schemes found, Chemical and Engineering News, Jan. 1993, pp. 6 and 7.*
Keim et al., *The Methanol–to–Gasoline (MTG) Process: Status Report on 100 BPD Fluid Bed Pilot Plant*, C–16, pp.2–160 –2–166.
Chang, "Methanol Conversion to Light Olefins," Catal. Rev.–Sci. Eng., 26(3&4), 323–345 (1984).
Kaeding et al., "Production of Chemicals from Methanol," Journal of Catalysis 61, 155–164 (1980).
Barger et al., "Converting Natural Gas to Ethylene and Propylene by the UOP/Hydro MTO Process," 12th International Zeolite Conference Materials Research Society p. 567–573 (1999).

* cited by examiner

*Primary Examiner*—Rosalynd Keys

(57) ABSTRACT

The invention discloses a method for converting alkane to oxygenate which comprises the following steps: (i) contacting an alkane-containing gas with non-metal, regenerable, electrophile ions in a concentrated sulfuric acid medium under conditions sufficient to provide electrophilicly activated alkane and reduced electrophile ions; (ii) contacting said electrophilicly activated alkane with sulfate to form a sulfate ester; (iii) exposing the sulfate ester to hydrolyzing conditions sufficient to convert it to oxygenate; and (iv) collecting the oxygenate.

11 Claims, 1 Drawing Sheet

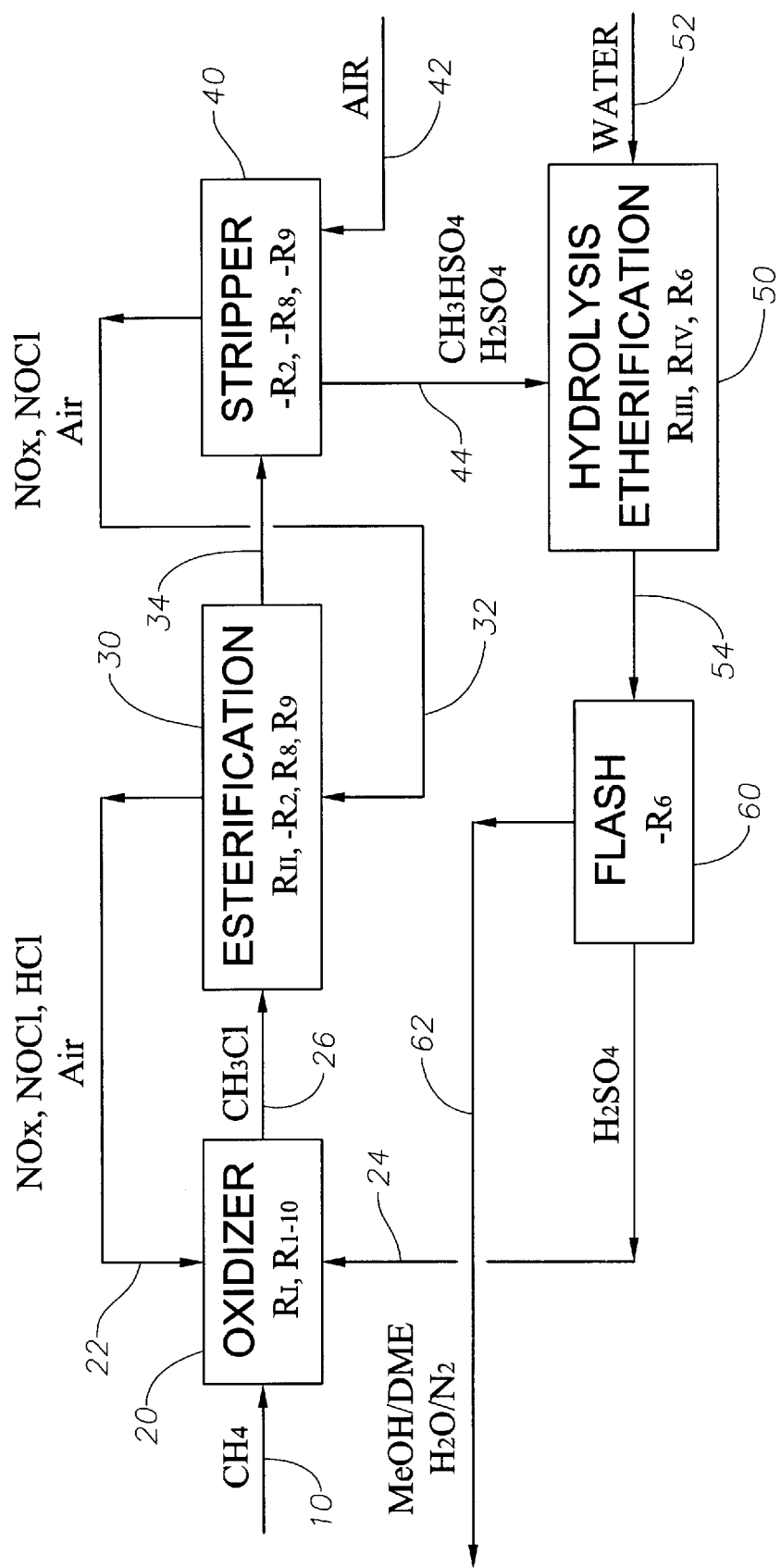

METHOD FOR CONVERTING ALKANES TO OXYGENATES

BACKGROUND OF THE INVENTION

This invention relates to utilizing alkane, e.g., methane, as a fundamental component for the production of oxygenates, especially alkanol and dialkylether, e.g., methanol and/or dimethylether. More particularly, the invention relates to a unique conversion scheme using electrophile ions, e.g., chloronium and/or nitrosonium ions to produce the oxygenates.

Natural gas is an abundant fossil fuel resource. Recent estimates place worldwide natural gas reserves at about $35 \times 10^{14}$ standard cubic feet, corresponding to the energy equivalent of about 637 billion barrels of oil.

A major source of methane is natural gas. Primary sources for natural gas are the porous reservoirs generally associated with crude oil reserves. From these sources come most of the natural gas used for heating purposes. Quantities of natural gas are also known to be present in coal deposits and are by-products of crude oil refinery processes and bacterial decomposition of organic matter. Natural gas obtained from these sources is generally utilized as a fuel at the site.

The composition of natural gas at the wellhead varies but the major hydrocarbon present is methane. For example, the methane content of natural gas may vary within the range of from about 40 vol. % to 95 vol. %. Other constituents of natural gas may include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

A significant portion of the known natural gas reserves is associated with fields found in remote, difficultly accessible regions. Many of these distant sources are not amenable to transport by pipeline. For example, sources that are located in areas requiring economically unfeasible pipeline networks or in areas requiring transport across large bodies of water are not amenable to transport by pipeline. This problem has been addressed in several ways. One such solution has been to build a production facility at the site of the natural gas deposit to manufacture one specific product. This approach is limited as the natural gas can be used only for one product, preempting other feasible uses. Another approach has been to liquefy the natural gas and transport the liquid natural gas in specially designed tanker ships. Natural gas can be reduced to 1/600th of the volume occupied in the gaseous state by such processing, and with proper procedures, safely stored or transported. These processes, which involve liquefying natural gas at a temperature of about $-162°$ C., transporting the gas, and revaporizing it, are complex and energy intensive.

Still another approach has been the conversion of natural gas to higher order hydrocarbons that can be easily handled and transported. The term "higher order hydrocarbon" refers to a hydrocarbon having at least two carbon atoms. In this way easily transportable commodities may be derived directly from natural gas at the wellhead. The conversion of natural gas to higher order hydrocarbons, especially ethane and ethylene, retains the material's versatility for use as precursor materials in chemical processing. Known processes are available for the further conversion of ethane and ethylene to other useful materials.

U.S. Pat. No. 4,199,533 discloses a process for converting methane to higher molecular weight hydrocarbons by using chlorine gas as a recyclable catalyst. The process produces ethylene as a major product along with hydrogen chloride, which is converted to chlorine for recycle in the system. Major drawbacks of the '533 process are the large amount of chlorine required, the necessity of regenerating chlorine from hydrogen chloride to maintain an economically viable system, and the need to use operating temperatures in excess of 1000° C. to produce ethylene. Additionally, the required chlorine is corrosive under such operating conditions.

It is known to use chloronium ion in treating hydrocarbon conversion catalysts. For example, U.S. Pat. No. 3,950,270 to Paynter et al. discloses iridium-containing reforming catalysts containing iron or bismuth wherein agglomerated iridium is readily dispersible by combining iron and bismuth with halide, e.g., chlorine, to provide a chloronium ion which reacts with iridium oxide, $IrO_2$, to form $IrO_2Cl$, which is more readily redispersed.

Another process for converting natural gas involves formation of methanol. For offshore and other difficult gas producing locations, it is preferable to provide a process which is simple to operate. Because methanol production from natural gas is the simplest way to convert gas to liquid, it is highly desirable for on-site use. U.S. Pat. No. 3,898,057 to Moller et al. discloses a process for converting natural gas to a mixture of carbon monoxide and hydrogen at the site of production, converting the mixture to methanol, and transporting the methanol to a place of consumption where it is burnt or reconverted into methane. However, more efficient ways of converting methane to methanol would be highly desirable.

The electrophilic activation of methane in the presence of metal complexes such as (bipyridinium)$PtCl_2$ has been disclosed. "Platinum Catalysts for the High-Yield Oxidation of Methane to a Methanol Derivative", Roy A. Periana, Douglas J. Taube, Scott Gamble, Henry Taube, Takashi Satoh, and Hiroshi Fujii, *Science* Apr. 24, 1998; 280: 560–564. However, the reaction rate in such systems is low, the regenerability and stability of the metal complexes is questionable, and it has not been proven that these reactions are truly catalytic and not stoichiometric in the metal complex. In contrast, a method which utilizes non-metal electrophiles would be desirable, particularly if such electrophiles were readily regenerable.

SUMMARY OF THE INVENTION

The present invention provides a method for converting alkanes, e.g., methane, to oxygenates, e.g., alkanols and/or dialkylethers. This method comprises electrophilicly activating alkane using electrophilic ions, e.g., halonium, such as chloronium, in combination with nitrosonium and/or nitronium, and substituting the activated methane with sulfate to provide a sulfate ester intermediate which is hydrolyzed to alkanol and/or dialkylether.

The present invention provides a method for converting alkane to oxygenate. The method comprises the following steps: (i) contacting an alkane-containing gas with nonmetal, regenerable, electrophile ions in a concentrated sulfuric acid medium under conditions sufficient to provide electrophilicly activated alkane and reduced electrophile ions; (ii) contacting said electrophilicly activated alkane with sulfate to form a sulfate ester; (iii) exposing said sulfate ester to hydrolyzing conditions sufficient to convert it to oxygenate; and (iv) collecting said oxygenate.

BRIEF DESCRIPTION OF THE DRAWING

The FIGURE depicts a processing scheme of the present invention employing an apparatus which comprises an oxidizer, esterifier, stripper, hydrolyzer, etherifier, and flashing unit.

DETAILED DESCRIPTION OF THE INVENTION

The present invention provides a method for converting alkane, e.g., methane and ethane, to higher hydrocarbons, utilizing reaction sets I, II, I+II and III as follows:

$$CH_4 + Cl_2 \rightarrow CH_3Cl + HCl \qquad (I)$$

$$CH_3CL + NOHSO_4 \rightarrow CH_3HSO_4 + NOCl$$

and $$2HCl + \tfrac{1}{2}O_2 \rightarrow Cl_2 + H_2O \qquad (II)$$

$$NOCl + H_2SO_4 \rightarrow NOHSO_4 + HCl$$

The resulting sulfate ester is hydrolyzed, e.g., by addition of steam.

$$CH_4 + H_2SO_4 + \tfrac{1}{2}O^2 \rightarrow CH_3HSO_4 + H_2O \qquad (I+II)$$

$$CH_3HSO_4 + H_2O \rightarrow CH_3OH + H_2SO_4 \qquad (III)$$

to provide a net oxidation of alkane:
Net:

$$CH_4 + \tfrac{1}{2}O_2 \rightarrow CH_3OH$$

Without wishing to be bound by any theory, it is theorized that the present method utilizes electrophilic alkane activation using halonium, e.g., i) chloronium, with nitrosonium and/or nitronium electrophiles ($E^+$) or ii) nitrosonium and/or nitronium electrophiles alone. Chloronium (along with chloride) can exist in equilibrium with elemental chlorine, which may have but a transient existence. The electrophiles, in the presence of a source of sulfate, e.g., sulfuric acid, produce electrophilicly activated alkane, RH→$E^+$, e.g., $CH_4$→$E^+$. The electrophilicly activated alkane is concurrently substituted by sulfate from the reaction medium, e.g., concentrated sulfuric acid (reaction set I). The resulting sulfate ester is hydrolyzed, possibly by addition of steam in a separate step, to alkanol and/or dialkyl ether (reaction set III). Water is removed from the reaction by any suitable means, e.g., adiabatic flashing. Regeneration of the electrophile can be carried out by any suitable method, e.g., air-oxidation of the (halonium)/(nitrosonium and/or nitronium) electrophile at a suitable point in the process stream (reaction set II). The equilibrium is displaced to the right as water of reaction is absorbed by the concentrated sulfuric acid medium.

In another aspect, the present invention relates to a method of converting alkane to oxygenate. This method comprises the following steps: (i) contacting an alkane-containing gas with non-metal, regenerable, electrophile ions in a concentrated sulfuric acid medium under conditions sufficient to provide electrophilicly activated alkane and reduced electrophile ions; (ii) contacting the electrophilicly activated alkane with sulfate to form a sulfate ester; (iii) exposing the sulfate ester to hydrolyzing conditions sufficient to convert it to oxygenate; and (iv) collecting the oxygenate. Steps (i) and (ii) can be carried out concurrently.

The oxygenate can be selected from the group consisting of alkanol and dialkylether, preferably alkanol. The alkanol is selected from the group consisting of methanol, ethanol, 1-propanol, and 2-propanol, with methanol especially preferred. The dialkylether is selected from the group R—O—R' wherein R and R' are individually selected from the group consisting of methyl, ethyl, n-propyl and isopropyl, e.g., dimethylether, diethylether and di-i-propylether, with dimethylether being especially preferred. The alkane employed can be selected from $C_{1\ to\ 4}$ alkanes, e.g., the group consisting of methane, ethane and propane, with methane especially preferred. In a highly preferred embodiment of the present method, the alkane comprises methane, the alkanol comprises methanol and the dialkylether comprises dimethylether.

The electrophile ions suited to use in the present invention are non-metal, regenerable electrophile ions selected from the group consisting of chloronium, bromonium, iodonium, nitrosonium and nitronium ions. Chloronium, nitrosonium and nitronium ions are especially preferred.

Hydrolyzing can be carried out by addition of steam in a separate step.

Water can be removed from step iii) by adiabatic flashing or other water removal processes, including, distillation.

The reduced electrophile ions which are made during the method of the present invention can be regenerated by contacting with an oxidizing agent.

Suitable oxidizing agents include air, enriched air, and oxygen, with air being especially preferred.

In still another embodiment of the present invention, alkane functionalization can be carried out by a process which uses nitrogen oxide electrophiles such as nitrosonium and/or nitronium, in the absence of halonium. The process can use transition metal ions such as Group IIB ions, e.g., Zn, Cd, and Hg ions, to provide an electron acceptor from the alkyl radical produced. This procedure, exemplified with methane as alkane is set out below:

$$CH_4 + NO_2 = [CH_3\cdot] + HONO \qquad \text{I.}$$

$$[CH_3\cdot] + M^{n+} = [CH_3^+] + M^{(n-1)+} \qquad \text{II.}$$

$$[CH_3^{3\circ}] + HSO_4^- = CH_3HSO_4 \qquad \text{III.}$$

$$CH_3HSO_4 + H_2O = CH_3OH/DME + H_2SO_4 \qquad \text{IV.}$$

$$HONO + M^{(n-1)+} + H^+ + \tfrac{1}{2}O_2 = NO_2 + M^{n+} + H_2O \qquad \text{V.}$$

$$CH_4 + \tfrac{1}{2}O_2 = CH_3OH + H_2O$$

$M^{n+}$=Group IIB, or transition metal, ions, where n is an integer from 1 to 8.

In step I, methane is reacted with an oxide, or mixed oxides, of nitrogen in the presence of a metal ion and sulfuric acid. While not wishing to be bound by theory, a possible mechanism is proposed, wherein the nitrogen oxides abstract hydrogen from methane, forming a reactive methyl radical and lower N-oxide. In step II, the radical undergoes a 1-electron transfer to the metal ion, forming methylium ion and lower valence metal ion. In step III, methylium reacts with bisulfate ion to yield a bisulfate ester which ester is hydrolyzed (possibly in a separate step) to MeOH/DME in step IV. Finally, the lower N-oxide and reduced metal ion is regenerated by reaction with air in step V.

In accordance with the Figure, a methane-containing feed is passed through line 10 to oxidizer 20 wherein methane and chlorine are reacted to form methyl chloride and hydrochloric acid (reaction set I). Recycled $NO_x$ gases, nitrosyl chloride (NOCl), HCl, and air are added to the oxidizer through line 22 and sulfuric acid is added through line 24. Additional side reactions $R_{1-8}$, may occur in the oxidizer 20 as follows:

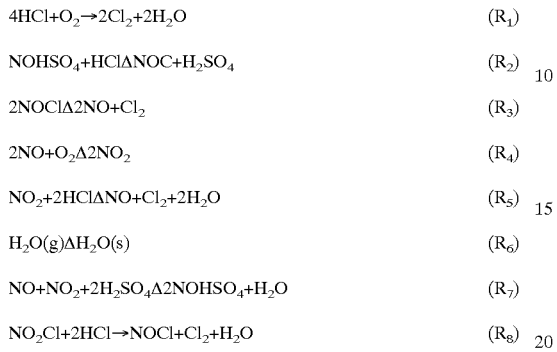

Methyl chloride (or chloromethane) effluent is passed from the oxidizer 20 through line 26 to esterifier 30 wherein methyl chloride and $NOHSO_4$ are reacted to form alkylsulfate ester $CH_3HSO_4$ and NOCl. Stripped $NO_x$ gases, nitrosyl chloride (NOCl) and air (taken from the effluent of stripper 40) are added to the esterifier 30 through line 32. Additional side reactions —$R_2$, and $R_7$ (—R indicating a leftward progression of the reaction) may also take place in stripper 40. Esterifier 30 effluent is passed through line 34 to stripper 40 which receives air via inlet 42.

Side reactions —$R_2$, and —$R_7$ may also take place in the stripper 40. $CH_3HSO_4$ and $H_2SO_4$ are removed from stripper 40 via line 44 to a combined hydrolysis and etherification unit 50 to which a source of water, e.g., steam, ($R_6$) is added through line 52 causing hydrolysis of $CH_3HSO_4$ to form $CH_3OH$+sulfuric acid. Two moles of the resulting methanol can react to form one mole of dimethylether and one mole of water. The products of the combined hydrolysis and etherification unit 50 are conducted via line 54 to flashing unit 60 which flashes off methanol, dimethylether, water and nitrogen as overhead via line 62. Sulfuric acid is taken off through line 24 and cycled to oxidizer 20.

Ideally, $NO_x$ is recycled completely and never escapes the system; however, some loss of $NO_x$ is expected and $NO_x$ equivalents can be made up by adding commercially acceptable $NO_x$ sources, e.g., nitrosylsulfuric acid or nitric acid. Similarly, chlorine is ideally completely recycled; however, expected loses can be made up by adding chlorine sources, e.g., HCl.

One skilled in the art will appreciate that modifications may be made to the present invention without departing from the spirit and scope of the present invention. The embodiments described herein are meant to be illustrative only and should not be taken as limiting the invention, which is defined in the following claims.

What is claimed is:

1. A method for converting alkane to oxygenate which comprises the following steps:

i) contacting an alkane-containing gas with non-metal, regenerable, electrophile ions in a concentrated sulfuric acid medium under conditions sufficient to provide electrophilicly activated alkane and reduced electrophile ions, wherein at least one of said electrophile ions is selected from the group consisting of chloronium, nitrosonium, and nitronium;

ii) contacting said electrophilicly activated alkane with sulfate to form a sulfate ester;

iii) exposing said sulfate ester to hydrolyzing conditions sufficient to convert it to oxygenate; and iv) collecting said oxygenate.

2. The method of claim 1 wherein said oxygenate is selected from the group consisting of alkanol and dialkylether.

3. The method of claim 2 wherein said alkane is selected from the group consisting of methane, ethane and propane, said alkanol is selected from the group consisting of methanol, ethanol, 1-propanol, and 2-propanol, and said dialkylether is selected from the group consisting of dimethylether, diethylether and di-i-propylether.

4. The method of claim 3 wherein said alkane comprises methane, said alkanol comprises methanol and said dialkylether is dimethylether.

5. The method of claim 1 wherein said steps i) and ii) are carried out concurrently.

6. The method of claim 1 wherein said hydrolyzing conditions comprise steaming.

7. The method of claim 1 wherein said water is removed from step iii) by adiabatic flashing.

8. The method of claim 1 wherein said reduced electrophile ions are regenerated by contacting with an oxidizing agent.

9. The method of claim 7 wherein said oxidizing agent is air.

10. The method of claim 1 wherein said electrophile ions comprise chloronium and at least one of the group consisting of nitrosonium, and nitronium ions.

11. The method of claim 1 wherein said electrophile ions are selected from the group consisting of nitrosonium and nitronium ions.

* * * * *